United States Patent [19]

Koerwer

[11] 4,280,832

[45] Jul. 28, 1981

[54] PYRIDYLOXY-PHENOXYALKANE CARBOXYLIC ACIDS AND DERIVATIVES AS SUGAR ENHANCERS FOR PLANTS

[75] Inventor: John F. Koerwer, Perkasie, Pa.

[73] Assignee: Union Carbide Corporation, New York, N.Y.

[21] Appl. No.: 133,851

[22] Filed: Mar. 25, 1980

[51] Int. Cl.$^3$ ............................................. A01N 43/40
[52] U.S. Cl. ........................................................ 71/94
[58] Field of Search ............................................ 71/94

[56] References Cited

U.S. PATENT DOCUMENTS 4,115,102  9/1978  Takahashi et al. ...................... 71/94

FOREIGN PATENT DOCUMENTS 862325  6/1978  Belgium .

Primary Examiner—Catherine L. Mills
Attorney, Agent, or Firm—William Raymond Moran

[57] ABSTRACT

A method for increasing the sugar content of plants by applying to such plants an effective amount of a pyridyloxy-phenoxyalkane carboxylic acid or derivative thereof.

70 Claims, No Drawings

PYRIDYLOXY-PHENOXYALKANE CARBOXYLIC ACIDS AND DERIVATIVES AS SUGAR ENHANCERS FOR PLANTS

FIELD OF THE INVENTION

This invention relates to a novel method for increasing the sugar content of plants by applying to such plants an effective amount of a pyridyloxy-phenoxyalkane carboxylic acid or derivative thereof.

BACKGROUND OF THE INVENTION

Certain pyridyloxy-phenoxyalkane carboxylic acids and derivatives thereof are disclosed in U.S. Pat. No. 4,115,102 to have a strong selective herbicidal activity toward gramineous plants but to affect broad-leafed plants to only a slight extent. Said patent further discloses that such compounds can be applied to kill gramineous weeds on farms where gramineous crops are cultivated if they are applied in small dosage (5–20 g/a) and the plants have grown to some degree.

Belgian Pat. No. 862,325, on the hand, discloses derivatives of pyridyloxy-phenoxyalkane carboxylic acids having herbicidal and phytoregulatory action to selectivity control plants harmful to crops and to selectively regulate the growth of plants (including gramineous plants and grains, and dicotyledons).

However, neither patent discloses any other biological action of such compounds. In particular, neither patent discloses the use of such compounds to increase the sugar content of plants such as sugarcane (*Saccharum officinerum*) or sorghum (*Sorghum vulgare*). Increased sugar content, of course, increases the value of such plants.

SUMMARY OF THE INVENTION

In accordance with the present invention, it has now been discovered that certain pyridyloxy-phenoxyalkane carboxylic acids and derivatives thereof can be employed to increase the sugar content of plants when applied to such plants from 1 to 7 weeks prior to harvesting in an amount insufficient to exert a herbicidal effect. As a result, an earlier accumulation and significant increase in the sugar content of plants such as sugarcane (*Saccharum officinerum*) and sorghum (*Sorghum vulgare*) can be effected. The resulting plants are of greater value, of course, than the untreated plants.

DETAILED DESCRIPTION OF THE INVENTION

The pyridyloxy-phenoxyalkane carboxylic acids and derivatives useful as plant sugar enhancers according to the present invention can be represented by the formula

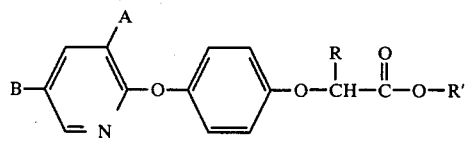

wherein:
A is a hydrogen atom or a halogen atom,
B is a hydrogen atom or a halogen atom,
R is a hydrogen atom or a methyl group, and
R' is a hydrogen atom, an alkyl group having from 1 to 4 carbon atoms, or a cation;

provided, however, that either A or B must be a halogen atom.

When R' is an alkyl group in the above formula, it can be either straight or branched chain, e.g., methyl, ethyl, isopropyl, tert.-butyl, and the like, and may be substituted with one or more of a variety of substituents, such halogen or hydroxyl. When halogen is present, it is preferably chlorine. When R' represents a cation in the formula, it is preferably an ammonium radical, an alkali metal, or an alkaline earth metal, but can be any other agriculturally acceptable cation.

The pyridyloxy-phenoxyalkane carboxylic acids and pyridyloxy-phenoxyalkane carboxylic acid derivatives employed in the present invention are known compounds and can be prepared by conventional synthesis methods well known to those skilled in the art. The preparation of such compounds is disclosed, for example, in the U.S. Pat. No. 4,115,102, which is hereby incorporated herein by reference.

The compounds employed as plant sugar enhancers in the method of this invention are applied to the plant from 1 to 7 weeks prior to harvesting, preferably from 3 to 5 weeks prior to harvesting. Such compounds should be applied in an amount sufficient to increase the sugar content of the plant, i.e., an effective amount should be employed. As mentioned hereinbefore, however, the amount employed should be insufficient to exert a herbicidal effect on the plant. The proper amount is determined by and dependent upon such factors as the particular compound employed, the method of application, the particular plant species, the state and condition of growth of the plant, and the climatic conditions. Generally, from about 1/16 lb./acre to about 1 lb./acre, preferably from about ⅛ lb./acre to about ½ lb./acre, are employed.

The pyridyloxy-phenoxyalkane carboxylic acids or derivatives employed in the method of this invention can be applied to mature plants in any suitable form, e.g., as solutions, emulsions, suspensions, dust formulations, and the like. Such compositions generally contain the active compound in an amount of from about 0.03 percent by weight to about 13 percent by weight, preferably from about 0.3 percent by weight to about 0.6 percent by weight. Both liquid compositions and dust formulations may be conveniently applied from either a ground rig or from an aircraft.

The preferred carrier for the active compounds employed in the method of this invention is water. When the active compound is water-soluble, it can be simply dissolved in an amount of water sufficient to give the desired concentration and sprayed on the plants. If desired, a suitable wetting agent may be added to the solution to improve wetting of the foliage and to increase the penetration of the solution into the tissue of the plant. Preferred wetting agents include anionic or non-anionic surfactants such as sodium alkylsulfates, sodium alkylbenzenesulfonates, sodium ligninsulfonates, polyoxyethylene lauryl ethers, polyoxyethylene alkylaryl ethers, polyoxyethylene fatty acid esters, and polyoxyethylene sorbitan fatty acid esters. Such wetting agents generally do not exceed 1 percent by volume of the final spray solution, and preferably comprise about 0.1 percent to about 0.5 percent of the final spray volume.

Those active compounds which are not sufficiently water-soluble for conventional formulation into aqueous solutions can be prepared as liquid emulsions by dissolving the compounds in a small amount of an agriculturally acceptable solvent and then adding an emulsifier and water. Suitable solvents include n-hexane, toluene, xylene, naphtha, isophorone, dimethylformamide, and the like. Hydrocarbon oils, including paraffin oils, aromatic oils and asphaltic oils, can also be employed, although highly-aromatic oils are preferred, particularly highly-aromatic petroleum-base oils. Suitable emulsifiers include sodium ligninsulfonate, sodium 2,2'-dinaphthylmethane-6,6'-disulfonate, sodium dibutylsulfonate, and sodium oleylmethyllaurate.

Alternatively, these compounds may be formulated into wettable powders which can be dispersed in water by compounding them with conventional excipients such as fillers, wetting agents, dispersing agents, and the like. The wetting agents and emulsifiers mentioned above can be employed in this application. Suitable fillers include vermiculite, attaclay, talc, diatomaceous earth, pyrophillite, kaolin, bentonite, and the like.

If desired, the active compounds employed in the method of this invention can be compounded with finely-divided, solid excipients, such as those named above, and applied to the plants as a dust formulation.

If desired, two or more active compounds can be employed in the method of the present invention. Should an admixture be employed, there is no prescribed ratio in which each particular compound must be present. The concentration of the admixture need only be within the concentration range of active material prescribed herein, and the rate of application of the admixture should be within the effect range prescribed herein.

The following examples are set forth for purposes of illustration so that those skilled in the art may better understand the invention. Tt should be understood, however, that they are exemplary only, and should not be construed as limiting this invention in any manner.

EXAMPLE 1

Sodium 2-[4-3,5-dichloro-2-pyridyloxy)phenoxy]-propionate was applied to two varieties of sugarcane, CP65–357 and a "Texas" variety, which were 9 to 10 months old and had 15 to 18 internodes each. Application was made at the rate of one ounce acid equivalent of compound per acre by depositing an aqueous solution of the compound, by means of a syringe, onto the spindle area at the top of the last visible dewlap of 2 stalks of the CP65-357 variety and 8 stalks of the "Texas" variety. Each stalk was treated with 0.6 ml. of a solution containing 1 mg. of the compound in this manner. (A dewlap is the junction between the blade of the leaf and the sheath which clasps the stalk).

The procedure was then repeated at a rate of two and four ounce acid equivalents of compound per acre by treating a like number of stalks with 0.6 ml. amounts of a solution containing 2 and 4 mg. of the compound, respectively.

The stalks were harvested 5 weeks after such treatment. The top 11 internodes of each stalk were then removed and analyzed for brix by means of a refractometer and for reducing sugars using Benedict's copper reduction reaction (Benedict, S. R., J. Biol. Chem., 5:485, 1909). Sucrose content was then calculated from the difference between these values. The average results obtained for each variety of sugarcane treated in this manner are set forth below in Table I and compared to like untreated plants.

TABLE I

| Rate of Application Ounces/Acre | Variety of Sugarcane | |
| --- | --- | --- |
| | CP65-357 % Sucrose | Texas % Sucrose |
| 1 | 11.8 | 13.8 |
| 2 | 18.4 | 17.4 |
| 4 | 18.3 | 14.0 |
| Untreated | 8.9 | 11.0 |

EXAMPLE 2

Each of the compounds listed below in Table II were applied to high sucrose sorghum (variety-Ramada) at the eight (8) leaf stage of growth at the rate of 8 ounces acid equivalent of compound per acre. Application was made by spraying 10 ml. of an aqueous solution or emulsion of each particular compound upon 5 stalks of sorghum (a rate of 100 gallons per acre). The solutions and emulsions were prepared by dissolving each compound and a surfactant in a solvent and diluting the solution with water to a final volume of 10 ml.

The sorghum was harvested 12 days after such treatment. The sap of each stalk was then analyzed for brix by means of a refractometer and for reducing sugars using Benedict's copper reduction reaction. Sucrose content was then calculated from the difference between these values. The average results obtained for each compound employed are set forth in Table II and compared to like untreated sorghum.

TABLE II

| Compound | Average Sugar Content, % |
| --- | --- |
| Sodium 2-[4-(3,5-dichloro-2-pyridyloxy)phenoxy]-propionate | 8.7 |
| 2-[4-(3,5-dichloro-2-pyridyloxy)phenoxy]propionic acid | 8.1 |
| Ethyl 2-[4-(5-bromo-2-pyridyloxy)phenoxy]propionate | 10.2 |
| Butyl 2-[4-(5-iodo-2-pyridyloxy)phenoxy]propionate | 9.6 |
| 2-[4-(5-iodo-2-pyridyloxy)phenoxy]propionic acid | 8.2 |
| Ethyl 2-[4-(3,5-dichloro-2-pyridyloxy)phenoxy]-propionate | 8.4 |
| Untreated | 5.3 |

EXAMPLE 3

Each of the compounds listed below in Table III were applied to 4½ month old high sucrose sorghum (variety-Ramada) at the rate of 4 ounces acid equivalent of compound per acre. Application was made by spraying 20 foot long rows of sorghum (spaced 6–8 inches apart) with an aqueous solution or emulsion of each particular compound at a rate of 40 gallons per acre. The solutions and emulsions were prepared by dissolving each compound and a surfactant in a solvent and diluting the solution with water.

Ten stalks of sorghum of each replication were harvested 3 weeks after such treatment, and another 10 stalks of each replication were harvested 7 weeks after treatment. The sap of each stalk was analyzed for brix by means of a refractometer and for reducing sugars using Benedict's copper reduction reaction. Sucrose content was then calculated from the difference between these values. The average results obtained for each compound employed for both the 3-week and 7-week harvests are set forth in Table III and compared to like untreated sorghum.

TABLE III

| Compound | Average Sugar Content, % | |
|---|---|---|
| | 3 Weeks | 7 Weeks |
| Sodium 2-[4-(3,5-dichloro-2-pyridyloxy)phenoxy]propionate | 10.8 | 12.5 |
| Ethyl 2-[4-(5-bromo-2-pyridyloxy)phenoxy]propionate | 12.5 | 13.1 |
| Butyl 2-[4-(5-iodo-2-pyridyloxy)phenoxy]propionate | 11.5 | 13.1 |
| Untreated | 7.8 | 11.8 |

What is claimed is:

1. A method for increasing the sugar content of plants which comprises applying to such plants from 1 to 7 weeks prior to harvesting an effective amount of a compound of the formula.

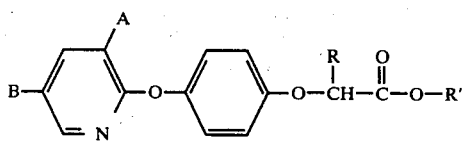

wherein:
A is a hydrogen atom or a halogen atom,
B is a hydrogen atom or a halogen atom,
R is a hydrogen atom or a methyl group, and
R' is a hydrogen atom, an alkyl group having from 1 to 4 carbon atoms, or a cation;
provided, however, that either A or B must be a halogen atom.

2. A method as in claim 1 wherein the compound is sodium 2-[4-(3,5-dichloro-2-pyridyloxy)phenoxy]propionate.

3. A method as in claim 1 wherein the compound is 2-[4-(3,5-dichloro-2-pyridyloxy)phenoxy]propionic acid.

4. A method as in claim 1 wherein the compound is ethyl 2-[4-(5-bromo-2-pyridyloxy) phenoxy]propionate.

5. A method as in claim 1 wherein the compound is butyl 2-[4-(5-iodo-2-pyridyloxy) phenoxy]propionate.

6. A method as in claim 1 wherein the compound is 2-[4-(5-iodo-2-pyridyloxy)phenoxy]propionic acid.

7. A method as in claim 1 wherein the compound is ethyl 2-[4-(3,5-dichloro-2-pyridyloxy)phenoxy]propionate.

8. A method as in any one of claims 2, 3 or 4 wherein application is made at a rate of from 1/16 lb./acre to 1 lb./acre.

9. A method as in any one of claims 5, 6 or 7 wherein application is made at a rate of from 1/16 lb./acre to 1 lb./acre.

10. A method as in any one of claims 2, 3 or 4 wherein application is made at a rate of from ⅛ lb./acre to ½ lb./acre.

11. A method as in any one of claims 5, 6 or 7 wherein application is made at a rate of from ⅛ lb./acre to ½ lb./acre.

12. A method as in claim 1 wherein the plants are sugarcane plants.

13. A method as in claim 12 wherein the compound is sodium 2-[4-(3,5-dichloro-2-pyridyloxy)phenoxy]propionate.

14. A method as in claim 12 wherein the compound is 2-[4-(3,5-dichloro-2-pyridyloxy)phenoxy]propionic acid.

15. A method as in claim 12 wherein the compound is ethyl 2-[4-(5-bromo-2-pyridyloxy)phenoxy]propionate.

16. A method as in claim 12 wherein the compound is butyl 2-[4-(5-iodo-2-pyridyloxy)phenoxy]propionate.

17. A method as in claim 12 wherein the compound is 2-[4-(5-iodo-2-pyridyloxy)phenoxy]propionic acid.

18. A method as in claim 12 wherein the compound is ethyl 2-[4-(3,5-dichloro-2-pyridyloxy)phenoxy]propionate.

19. A method as in any one of claims 13, 14 or 15 wherein application is made at a rate of from 1/16 lb./acre to 1 lb./acre.

20. A method as in any one of claims 16, 17 or 18 wherein application is made at a rate of from 1/16 lb./acre to 1 lb./acre.

21. A method as in any one of claims 13, 14 or 15 wherein application is made at a rate of from ⅛ lb./acre to ½ lb./acre.

22. A method as in any one of claims 16, 17 or 18 wherein application is made at a rate of from ⅛ lb./acre to ½ lb./acre.

23. A method as in claim 1 wherein the plants are sorghum plants.

24. A method as in claim 23 wherein the compound is sodium 2-[4-(3,5-dichloro-2-pyridyloxy)phenoxy]propionate.

25. A method as in claim 23 wherein the compound is 2-[4-(3,5-dichloro-2-pyridyloxy)phenoxy]propionic acid.

26. A method as in claim 23 wherein the compound is ethyl 2[4-(5-bromo-2-pyridyloxy)phenoxy]propionate.

27. A method as in claim 23 wherein the compound is butyl 2-[4-(5-iodo-2-pyridyloxy)phenoxy]propionate.

28. A method as in claim 23 wherein the compound is 2-[4-(5-iodo-2-pyridyloxy)phenoxy]propionic acid.

29. A method as in claim 23 wherein the compound is ethyl 2-[4-(3,5-dichloro-2-pyridyloxy)phenoxy]propionate.

30. A method as in any one of claims 24, 25, or 26 wherein application is made at a rate of from 1/16 lb./acre to 1 lb./acre.

31. A method as in any one of claims 27, 28 or 29 wherein application is made at a rate of from 1/16 lb./acre to 1 lb./acre.

32. A method as in any one of claims 24, 25 or 26 wherein application is made at a rate of from ⅛ lb./acre to ½ lb./acre.

33. A method as in any one of claims 27, 28 or 29 wherein application is made at a rate of from ⅛ lb./acre to ½ lb./acre.

34. A method as in any one of claims 1, 12 or 23 wherein application is made at a rate of from 1/16 lb./acre to 1 lb./acre.

35. A method as in any one of claims 1, 12 or 23 wherein application is made at a rate of from ⅛ lb./acre to ½ lb./acre.

36. A method as in claim 1 wherein applcation is made from 3 to 5 weeks prior to harvesting.

37. A method as in claim 36 wherein the compound is sodium 2-[4-(3,5-dichloro-2-pyridyloxy)phenoxy]propionate.

38. A method as in claim 36 wherein the compound is 2-[4-(3,5-dichloro-2-pyridyloxy)phenoxy]propionic acid.

39. A method as in claim 36 wherein the compound is ethyl 2-[4-(5-bromo-2-pyridyloxy)phenoxy]propionate.

40. A method as in claim 36 wherein the compound is butyl 2-[4-(5-iodo-2-pyridyloxy)phenoxy]propionate.

41. A method as in claim 36 wherein the compound is 2-[4-(5-iodo-2-pyridyloxy)phenoxy]propionic acid.

42. A method as in claim 36 wherein the compound is ethyl 2-[4-(3,5-dichloro-2-pyridyloxy)phenoxy]propionate.

43. A method as in any one of claims 37, 38 or 39 wherein application is made at a rate of from 1/16 lb./acre to 1 lb./acre.

44. A method as in any one of claims 40, 41 or 42 wherein application is made at a rate of from 1/16 lb./acre to 1 lb./acre.

45. A method as in any one of claims 37, 38 or 39 wherein application is made at a rate of from ⅛ lb./acre to ½ lb./acre.

46. A method as in any one of claims 40, 41 or 42 wherein application is made at a rate of from ⅛ lb./acre to ½ lb./acre.

47. A method as in claim 36 wherein the plants are sugarcane plants.

48. A method as in claim 47 wherein the compound is sodium 2-[4-(3,5-dichloro-2-pyridyloxy)phenoxy]-propionate.

49. A method as in claim 47 wherein the compound is 2-[4-(3,5-dichloro-2-pyridyloxy)phenoxy]propionic acid.

50. A method as in claim 47 wherein the compound is ethyl 2-[4-(5-bromo-2-pyridyloxy)phenoxy]propionate.

51. A method as in claim 47 wherein the compound is butyl 2-[4-(5-iodo-2-pyridyloxy)phenoxy]propionate.

52. A method as in claim 47 wherein the compound is 2-[4-(5-iodo-2-pyridyloxy)phenoxy]propionic acid.

53. A method as in claim 47 wherein the compound is ethyl 2-[4-(3,5-dichloro-2-pyridyloxy)phenoxy]propionate.

54. A method as in any one of claims 48, 49 or 50 wherein application is made at a rate of from 1/16 lb./acre to 1 lb./acre.

55. A method as in any one of claims 51, 52 or 53 wherein application is made at a rate of from 1/16 lb./acre to 1 lb./acre.

56. A method as in any one of claims 48, 49 or 50 wherein application is made at a rate of from ⅛ lb./acre to ½ lb./acre.

57. A method as in any one of claims 51, 52 or 53 wherein application is made at a rate of from ⅛ lb./acre to ½ lb./acre.

58. A method as in claim 36 wherein the plants are sorghum plants.

59. A method as in claim 58 wherein the compound is sodium 2-[4-(3,5-dichloro-2-pyridyloxy)phenoxy]-propionate.

60. A method as in claim 58 wherein the compound is 2-[4-(3,5-dichloro-2-pyridyloxy)phenoxy]propionic acid.

61. A method as in claim 58 wherein the compound is ethyl 2-[4-(5-bromo-2-pyridyloxy)phenoxy]propionate.

62. A method as in claim 58 wherein the compound is butyl 2-[4-(5-iodo-2-pyridyloxy)phenoxy]propionate.

63. A method as in claim 58 wherein the compound is 2-[4-(5-iodo-2-pyridyloxy)phenoxy]propionic acid.

64. A method as in claim 58 wherein the compound is ethyl 2-[4-(3,5-dichloro-2-pyridyloxy)phenoxy]propionate.

65. A method as in any one of claims 59, 60 or 61 wherein application is made at a rate of from 1/16 lb./acre to 1 lb./acre.

66. A method as in any one of claims 62, 63 or 64 wherein application is made at a rate of from 1/16 lb./acre to 1 lb./acre.

67. A method as in any one of claims 59, 60 or 61 wherein application is made at a rate of from ⅛ lb./acre to ½ lb./acre.

68. A method as in any one of claims 62, 63 or 64 wherein application is made at a rate of from ⅛ lb./acre to ½ lb./acre.

69. A method as in any one of claims 36, 47 or 58 wherein application is made at a rate of from 1/16 lb./acre to 1 lb./acre.

70. A method as in any one of claims 36, 47 or 58 wherein application is made at a rate of from ⅛ lb./acre to ½ lb./acre.

* * * * *